(12) United States Patent
Panzenbeck (10) Patent No.: US 12,426,853 B2
(45) Date of Patent: *Sep. 30, 2025

(54) ORIENTATION PINS FOR DEVICE USING RADIAL ULTRASOUND (71) Applicant: OLYMPUS MEDICAL SYSTEMS CORPORATION, Hachioji (JP)

(72) Inventor: Jason T. Panzenbeck, Redmond, WA (US)

(73) Assignee: OLYMPUS MEDICAL SYSTEMS CORPORATION, Tokyo (JP)

( * ) Notice: Subject to any disclaimer, the term of this patent is extended or adjusted under 35 U.S.C. 154(b) by 27 days.

This patent is subject to a terminal disclaimer.

(21) Appl. No.: 18/344,334

(22) Filed: Jun. 29, 2023

(65) Prior Publication Data
US 2023/0338007 A1 Oct. 26, 2023

Related U.S. Application Data (63) Continuation of application No. 17/325,926, filed on May 20, 2021, now Pat. No. 11,737,730, which is a
(Continued)

(51) Int. Cl.
A61B 8/00 (2006.01)
A61B 1/00 (2006.01)
(Continued)

(52) U.S. Cl.
CPC .......... *A61B 8/445* (2013.01); *A61B 1/00154* (2013.01); *A61B 8/0891* (2013.01);
(Continued)

(58) Field of Classification Search
CPC ... A61B 8/445; A61B 1/00154; A61B 8/0891; A61B 8/12; A61B 8/461; A61B 8/54;
(Continued)

(56) References Cited

U.S. PATENT DOCUMENTS 4,577,637 A 3/1986 Mueller, Jr.
5,596,990 A 1/1997 Yock et al.
(Continued)

FOREIGN PATENT DOCUMENTS

CN 106913332 7/2017
CN 110200654 A 9/2019
(Continued)

OTHER PUBLICATIONS

"U.S. Appl. No. 15/908,392, Non Final Office Action mailed Aug. 20, 2020", 8 pgs.
(Continued)

Primary Examiner — Sanjay Cattungal
(74) Attorney, Agent, or Firm — Dykema Gossett PLLC (57) ABSTRACT A system for determining orientation of a distal end of a catheter. The system includes a radial ultrasound system configured to generate images based on data received from a radial ultrasound probe. The system also includes a display device to present the generated images, a medical device, and a catheter system. The catheter system includes a flexible shaft having a first lumen configured to receive the radial ultrasound probe and a second lumen configured to receive the medical device, a cap portion having a longitudinal axis, and at least one orientation pin. The cap portion includes a third lumen configured to align with the first lumen, a fourth lumen configured to align with the second lumen, an exit port, and a ramp disposed between the fourth lumen and the exit port.

20 Claims, 12 Drawing Sheets

Related U.S. Application Data continuation of application No. 15/908,392, filed on Feb. 28, 2018, now Pat. No. 11,033,248.

(51) Int. Cl.
  *A61B 8/08* (2006.01)
  *A61B 8/12* (2006.01)

(52) U.S. Cl.
  CPC .............. *A61B 8/12* (2013.01); *A61B 8/461* (2013.01); *A61B 8/54* (2013.01); *A61B 8/4494* (2013.01); *A61B 8/468* (2013.01)

(58) Field of Classification Search
  CPC ... A61B 8/4494; A61B 8/468; A61B 1/00098; A61B 1/018; A61B 8/00; A61M 2025/0036; A61M 25/003; A61M 25/0108; A61M 25/0105
  See application file for complete search history.

(56) References Cited

U.S. PATENT DOCUMENTS

| | | | |
|---|---|---|---|
| 5,899,882 A * | 5/1999 | Waksman | A61N 5/1002 604/523 |
| 6,283,951 B1 | 9/2001 | Flaherty et al. | |
| 6,302,875 B1 | 10/2001 | Makower et al. | |
| 6,544,230 B1 * | 4/2003 | Flaherty | A61M 25/0108 604/164.12 |
| 6,942,680 B2 | 9/2005 | Grayzel et al. | |
| 8,545,434 B2 * | 10/2013 | Bosel | A61M 25/0021 604/523 |
| 9,955,994 B2 | 5/2018 | Nita | |
| 11,033,248 B2 | 6/2021 | Panzenbeck | |
| 11,737,730 B2 | 8/2023 | Panzenbeck | |
| 2001/0047165 A1 | 11/2001 | Makower et al. | |
| 2002/0010489 A1 | 1/2002 | Grayzel et al. | |
| 2002/0156521 A1 * | 10/2002 | Ryan | A61F 2/90 623/1.13 |
| 2008/0154345 A1 * | 6/2008 | Taylor | A61B 1/3137 607/93 |
| 2009/0005757 A1 * | 1/2009 | Taber | A61M 25/1002 600/585 |
| 2013/0296903 A1 | 11/2013 | Nita | |
| 2014/0135576 A1 * | 5/2014 | Hebert | A61B 1/05 600/109 |
| 2015/0209526 A1 | 7/2015 | Matsubara et al. | |
| 2016/0220302 A1 * | 8/2016 | Zarins | A61B 18/1482 |
| 2016/0279388 A1 * | 9/2016 | Barrish | A61M 25/1036 |
| 2016/0287210 A1 | 10/2016 | Chumo et al. | |
| 2017/0079519 A1 | 3/2017 | Sung et al. | |
| 2018/0028787 A1 * | 2/2018 | McNiven | A61F 2/24 |
| 2018/0049759 A1 | 2/2018 | Thomas | |
| 2019/0261946 A1 | 8/2019 | Panzenbeck | |
| 2021/0275139 A1 | 9/2021 | Panzenbeck | |

FOREIGN PATENT DOCUMENTS

| | | |
|---|---|---|
| DE | 102019103533 A1 | 8/2019 |
| GB | 2572852 A | 10/2019 |
| GB | 2572852 B | 3/2022 |
| JP | H11290324 A | 10/1999 |
| JP | 2001104315 A | 4/2001 |
| JP | 2002514111 | 5/2002 |
| JP | 2003088527 A | 3/2003 |
| JP | 2017506933 | 3/2017 |
| JP | 2017515620 A | 6/2017 |
| JP | 2019150567 A | 9/2019 |
| JP | 7305369 | 6/2023 |
| WO | WO-9846119 A1 | 10/1998 |
| WO | WO-2005023336 A2 | 3/2005 |
| WO | WO-2012014860 A1 | 2/2012 |
| WO | WO-2016154403 A1 | 9/2016 |

OTHER PUBLICATIONS

"U.S. Appl. No. 15/908,392, Notice of Allowance mailed Feb. 16, 2021", 8 pgs.

"U.S. Appl. No. 15/908,392, Response filed Jan. 15, 2021 to Non Final Office Action mailed Aug. 20, 2020", 8 pgs.

"U.S. Appl. No. 17/325,926, 312 Amendment filed Jun. 30, 2023", 6 pgs.

"U.S. Appl. No. 17/325,926, Amendment Under 37 C.F.R. § 1.312 filed Jun. 30, 2023", 6 pgs.

"U.S. Appl. No. 17/325,926, Corrected Notice of Allowability mailed Apr. 18, 2023", 5 pgs.

"U.S. Appl. No. 17/325,926, Non Final Office Action mailed Dec. 21, 2022", 10 pgs.

"U.S. Appl. No. 17/325,926, Notice of Allowance mailed Apr. 4, 2023", 9 pgs.

"U.S. Appl. No. 17/325,926, Response filed Mar. 16, 2023 to Non Final Office Action mailed Dec. 21, 2022", 6 pgs.

"Japanese Application Serial No. 2019-026429, Notification of Reasons for Rejection mailed Jan. 16, 2023", w/English Translation, 7 pgs.

"Japanese Application Serial No. 2019-026429, Response Filed Apr. 7, 2023 to Notification of Reasons for Rejection mailed Jan. 16, 2023", w/ English Claims, 7 pgs.

"United Kingdom Application Serial No. 1902556.8, Intention to Grant under Section 18(4) mailed Jan. 14, 2022", 4 pgs.

"United Kingdom Application Serial No. 1902556.8, Response filed Nov. 15, 2021 to Search Report mailed Sep. 14, 2021", 10 pgs.

"United Kingdom Application Serial No. 1902556.8, Search Report mailed Aug. 9, 2019", 5 pgs.

"United Kingdom Application Serial No. 1902556.8, Search Report mailed Sep. 14, 2021", 4 pgs.

"U.S. Appl. No. 17/325,926, PTO Response to Rule 312 Communication mailed Jul. 28, 2023", 2 pgs.

"Chinese Application Serial No. 201910145571.7, Office Action mailed Dec. 1, 2023", w English Translation, 16 pgs.

"Japanese Application Serial No. 2023-106392, Notification of Reasons for Refusal mailed Feb. 19, 2024", w English Translation, 8 pgs.

"Chinese Application Serial No. 201910145571.7, Response filed Apr. 3, 2024 to Office Action mailed Dec. 1, 2023", with English claims, 12 pgs.

* cited by examiner

ORIENTATION PINS FOR DEVICE USING RADIAL ULTRASOUND

CROSS-REFERENCE TO RELATED APPLICATIONS

This application is a Continuation of U.S. patent application Ser. No. 17/325,926, filed May 20, 2021, which is a Continuation of U.S. patent application Ser. No. 15/908,392, filed Feb. 28, 2018 and now issued as U.S. Pat. No. 11,033,248; the contents of which are incorporated herein by reference in their entireties.

BACKGROUND

The statements in this section merely provide background information related to the present disclosure and may not constitute prior art.

The tools that are currently available for the ultrasound visualization and sampling of peripheral lung tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (EBUS) miniprobe is then threaded through the guide sheath and used to determine the approximate location of the tumor.

Unfortunately, a peripheral tumor that is located off to one side of an airway (as opposed to one that is centered around an airway) has a substantially lower diagnostic yield in part due to the limitations of current radial EBUS technology, which allows the operator to discern the depth from the probe, but not the direction of the tumor. A sampling needle that extends off-axis from the length of the catheter and, therefore, requires a knowledge of rotational orientation of the needle and the sampling target. The radial ultrasound probe does not show the orientation of the needle to the lesion. The radial ultrasound image is a 360° image that allows the user to see a lesion, however, the user cannot tell if the needle is pointing towards the lesion.

SUMMARY

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various disclosed embodiments include illustrative devices, systems, and methods. As will be explained below, such embodiments can provide real-time sampling.

In an illustrative embodiment, a device including a flexible shaft having: a first lumen, and a second lumen; a cap portion having a longitudinal axis, and at least one orientation pin. The cap portion includes a third lumen configured to align with the first lumen, a fourth lumen configured to align with the second lumen, an exit port, and a ramp disposed between the second lumen, of the flexible shaft, and the exit port of the cap portion. The at least one orientation pin is positioned adjacent to the third lumen of the cap portion. At least a portion of the third lumen, the exit port, the ramp, and the at least one orientation pin intersect a plane perpendicular to the longitudinal axis.

In another illustrative embodiment, a system includes a radial ultrasound system, a display device, a medical device, and a catheter system. The radial ultrasound system includes a radial ultrasound probe and a signal processor configured to be in data communication with the radial ultrasound probe and generate one or more images based on data received from the radial ultrasound probe. The display device is configured to present the generated one or more images. The catheter system includes a flexible shaft, a cap portion having a longitudinal axis, and at least one orientation pin. The flexible shaft includes a first lumen and a second lumen. The cap portion includes a third lumen configured to align with the first lumen, a fourth lumen configured to align with the second lumen, an exit port, and a ramp disposed between the second lumen, of the flexible shaft, and the exit port of the cap portion. The at least one orientation pin is positioned adjacent to the third lumen of the cap portion. At least a portion of the third lumen, the exit port, the ramp, and the at least one orientation pin intersect a plane perpendicular to the longitudinal axis.

In another illustrative embodiment, a method includes providing a flexible shaft having a first lumen and a second lumen, providing a cap portion having a longitudinal axis, a third lumen configured to align with the first lumen, a fourth lumen configured to align with the second lumen, an exit port, and a ramp disposed between the second lumen and the exit port; and providing at least one orientation pin positioned adjacent to the third lumen of the cap portion; and attaching a distal end of the flexible shaft to the proximal end of the cap portion. At least a portion of the third lumen, the exit port, the ramp, and the at least one orientation pin intersect a plane perpendicular to the longitudinal axis Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
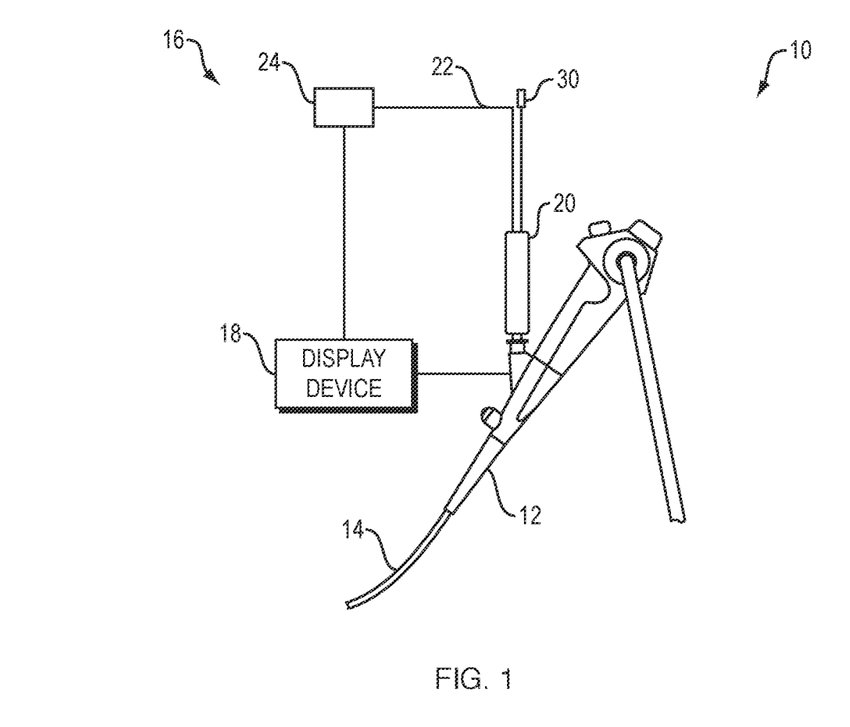
FIG. 1 illustrates an example of a bronchoscope system formed in accordance with an embodiment of the present invention.
Figure 2A:
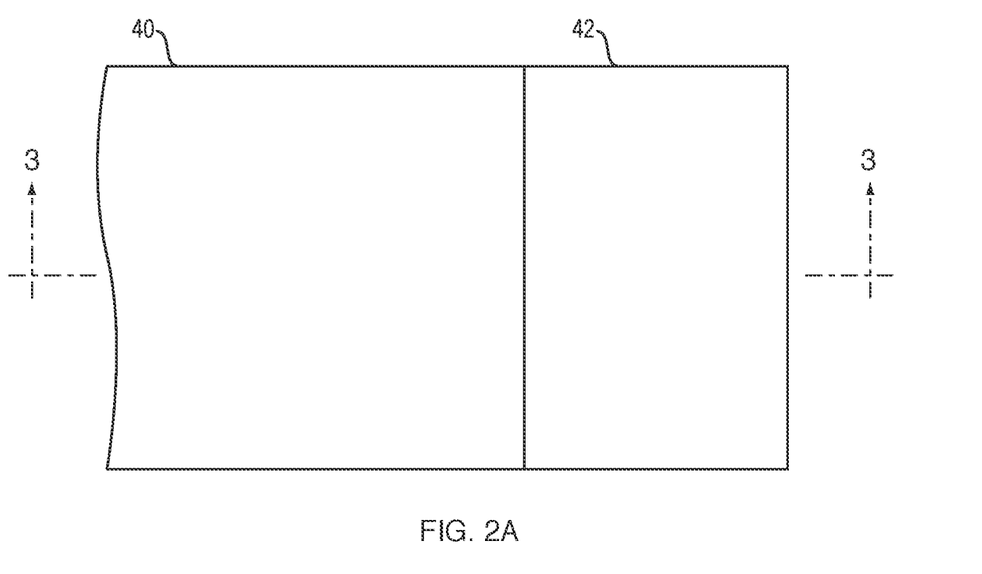
FIG. 2A is a side view of a distal end of a device formed in accordance with an embodiment of the present invention.
Figure 2B:
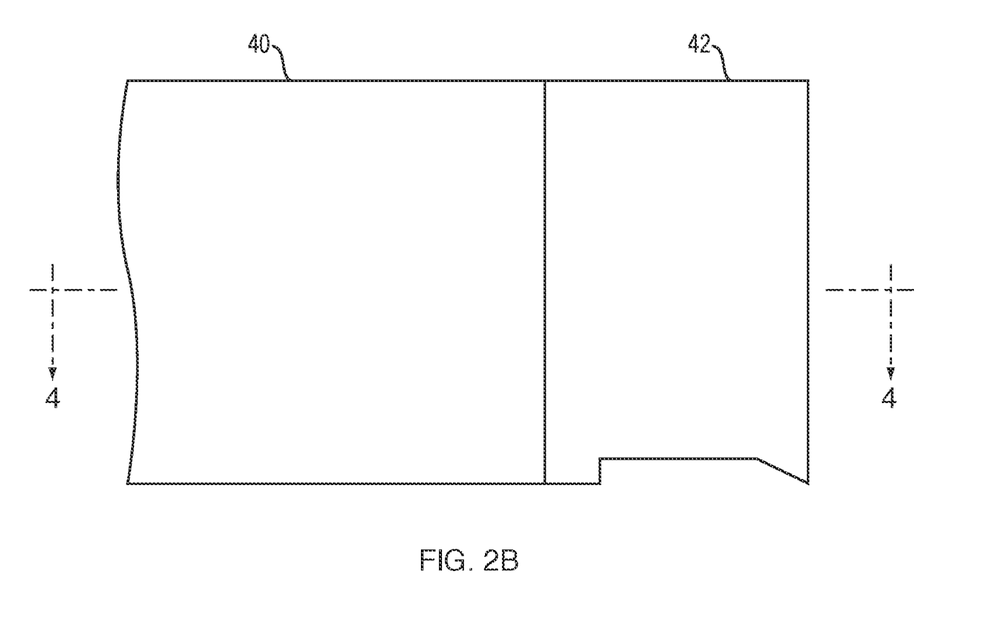
FIG. 2B is a side view of a distal end of the device of FIG. 2A rotated 90° about a longitudinal dimension.
Figure 3:
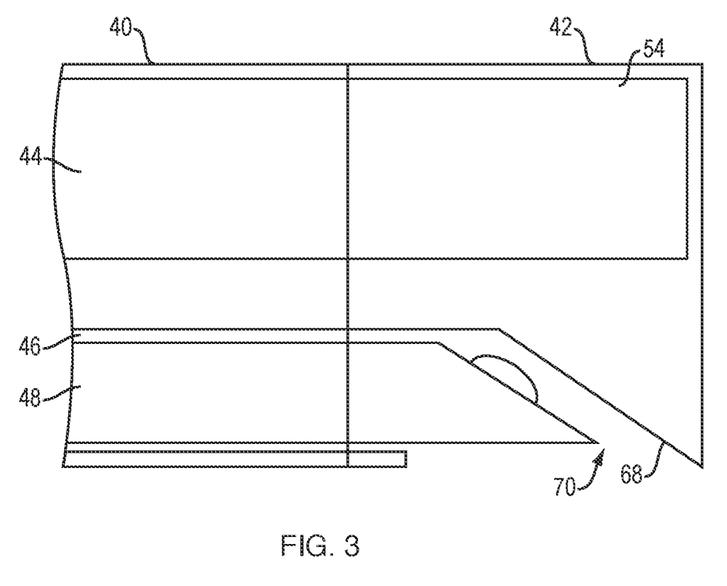
FIG. 3 is a cross-sectional view of a portion of the device shown in FIG. 2A.
Figure 4:
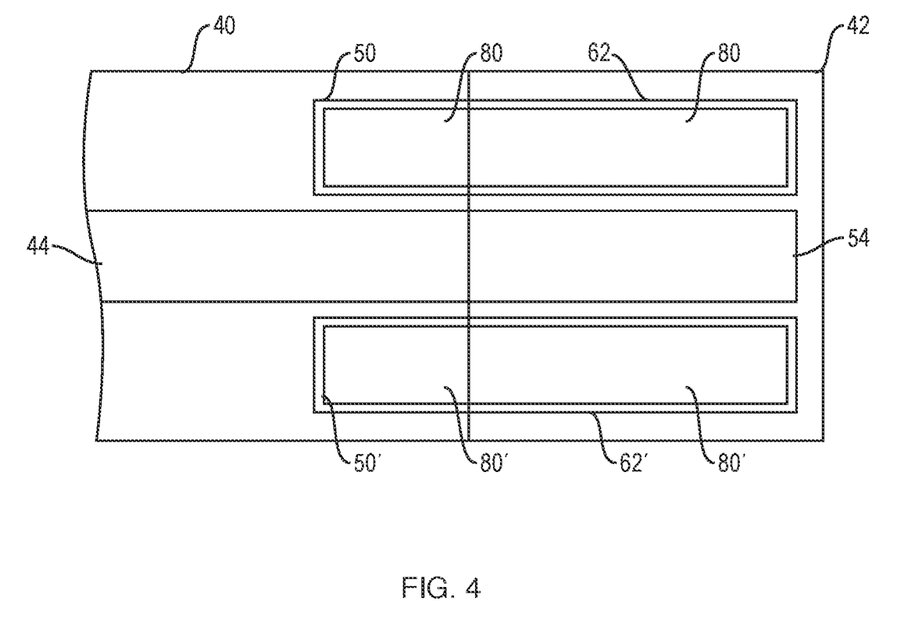
FIG. 4 is a cross-sectional view of a portion of the device shown in FIG. 2B.
Figure 5:
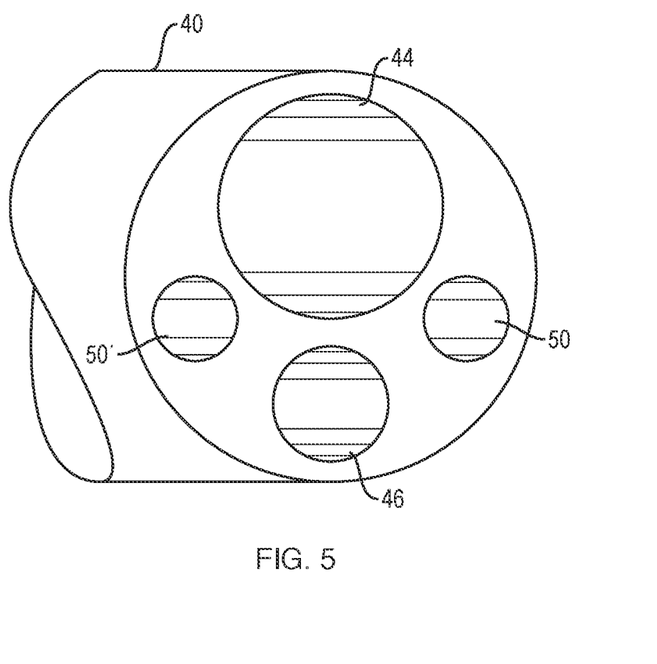
FIG. 5 is a perspective view of a portion of a distal end of a main catheter section of the device of FIG. 2A.

Referring now to FIG. 1, a bronchoscope system 10 includes a bronchoscope 12 with an insertion tube 14, a radial ultrasound system 16 and an access device 20. The radial ultrasound system 16 includes a signal processor 24, a display device 18 and a radial ultrasound probe 22. The radial ultrasound probe 22 and a medical device 30, such as a needle for sampling and/or medicant delivery, are received within the bronchoscope 12 via a handle component of the access device 20.

The display device 18 is in wired or wireless signal communication with the bronchoscope 12 and/or the signal processor 24. The display device 18 presents images generated based on information received from the bronchoscope 12 and/or the signal processor 24 that receives image information from a radial ultrasound transducer at the distal end of the radial ultrasound probe 22. A diagnostic bronchoscope (e.g., BF-X190 produced by Olympus®) is an example of the bronchoscope 12 and the radial endobronchial ultrasound (EBUS) miniprobes produced by Olympus® are examples of the radial ultrasound device 16.

The present invention uses echogenic orientation pins that are attached to the torqueable insertion device. The orientation pins are visible on the ultrasound image and thus alert the user to the rotational orientation of the distal end of the access device 20 and the needle relative to a target.

Figure 6:
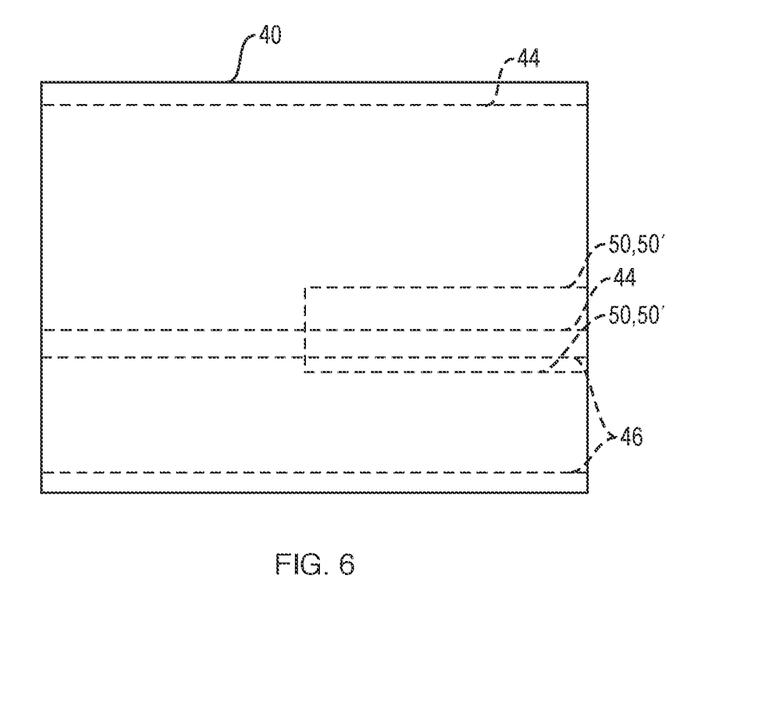
FIG. 6 is a side, x-ray view of the distal end of the main catheter section of FIG. 5.
Figure 7:
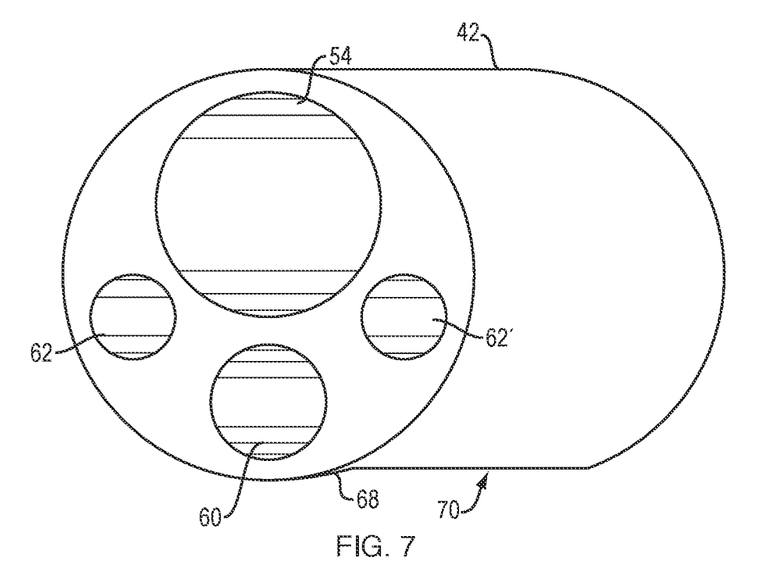
FIG. 7 is a perspective view of a proximal end of a cap section of the device of FIG. 2A.
Figure 8:
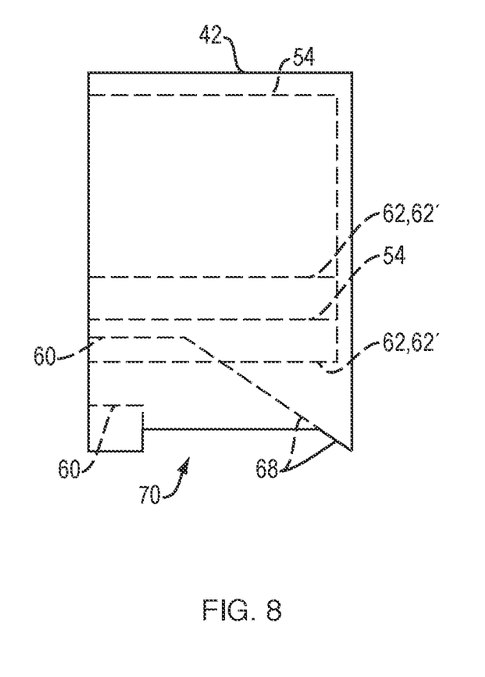
FIG. 8 is a side, x-ray view of the cap section of FIG. 7.

FIGS. 2-8 show an example of a distal end of the access device 20. The access device 20 includes a catheter portion 40 and a cap portion 42 at a distal end of the catheter portion 40. The catheter portion 40 extends from a handle portion (not shown). The catheter portion 40 includes a radial ultrasound lumen 44, a second lumen 46, a third lumen 50 and a fourth lumen 50'. The lumens 44, 46, 50, 50' are all accessible via a distal face of the catheter portion 40. The lumens 44, 46 extend to proximal ports (not shown) located at the handle portion, a port on a handle of the bronchoscope or other scope device, or at a position accessible by an operator. The lumens 44, 46 allow devices to be inserted from the proximal ends all the way to the distal end of the catheter portion 40. The radial ultrasound lumen 44 is sized to slidably receive a radial ultrasound probe (not shown). The second lumen 46 is sized to receive a medical device 48, such as a needle. In one embodiment, the third and fourth lumens 50, 50' extend only a predefined distance from the distal end of the catheter portion 40 (FIG. 6).

As shown in FIGS. 3, 4, 7 and 8, the cap portion 42 includes a first lumen 54, a second lumen 60, a third lumen 62 and a fourth lumen 62'. A first orientation pin 80 and a second orientation pin 80' each include a proximal end and a distal end. The proximal ends of the pins 80 and 80' are at least partially received within the third and fourth lumens 50 and 50' of the catheter portion 40. The distal ends of the pins 80, 80' are at least partially received within the third and fourth lumens 62, 62' of the cap portion 42. The pins 80, 80' may be pressure fitted into the lumens 50, 50', 62, 62' and/or are attached to one or more of the lumens 50, 50', 62, 62' with a reflow process, an adhesive or a welded joint. The pins 80, 80' may have a variety of shapes, such as round, oval, rectangular, with the lumens 50, 50', 62, 62' having comparable shapes. In one embodiment, the pin 80 is a different shape than the pin 80' with the lumens 50, 50', 62, 62' having corresponding shapes. The pins 80, 80' may include metal (e.g., stainless steel) or another material having ultrasound reflective properties. The pins 80, 80' may include reflective features, such as etchings or grooves, for increasing the echogenicity of the pins 80, 80'.

In one embodiment, the catheter is made of a braided (stainless steel) sheath with PTFE liners in the lumens and Pebax making up the body and the outer jacket. The cap may be made out of polycarbonate, PEEK, Ultem, or TPX (polymethylpentene).

In one embodiment, at least a proximal portion of the cap portion 42 is sized to be received within slots at the distal end of the catheter portion 40 or is sized to receive the distal end of the catheter portion 40, such that the pins 80, 80' are received within the third and fourth lumens 62, 62' and the first lumen 54 lines up with the radial ultrasound lumen 44 and the second lumen 60 lines up with the second lumen 46 of the catheter portion 40. Other methods of temporarily or permanently attaching the cap portion 42 to the distal end of the catheter portion 40 may be used. The distal end of the second lumen 60 of the cap portion 42 includes a side port 70 and a ramp 68. The ramp 68 causes the medical device 48 to deflect and exit the cap portion 42 through the side port 70. The lumens 54, 62, 62' may be closed/sealed or opened at their distal ends.

When a radial ultrasound probe is positioned within the cap portion 42, the radial ultrasound probe is able to produce a 360° image. The 360° image includes reflections of the orientation pins 80, 80'. Because the orientation pins 80, 80' are located on the same half of the first lumen 54, then any medical device passed through the second lumen 60 and out the side port 70 will interact with tissue visually located on the 360° image between the shortest arced distance between the reflections of the orientation pins 80, 80'. This is show by the example image of FIG. 9.

Figure 9:
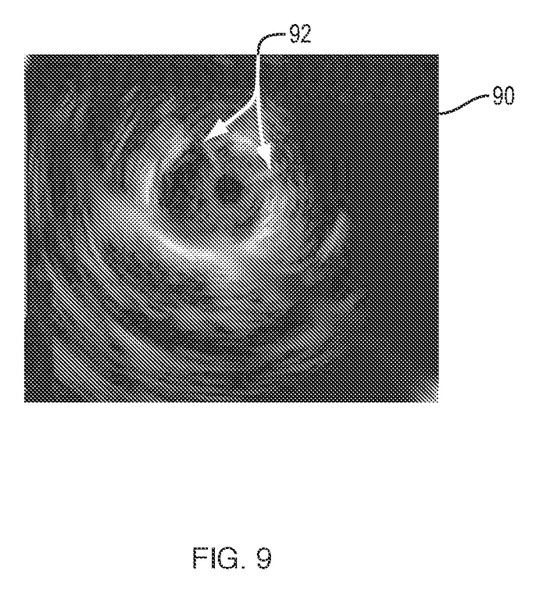
FIG. 9 is an exemplary image generated by a radial ultrasound probe used with the components shown in FIGS. 2-8.
Figure 10:
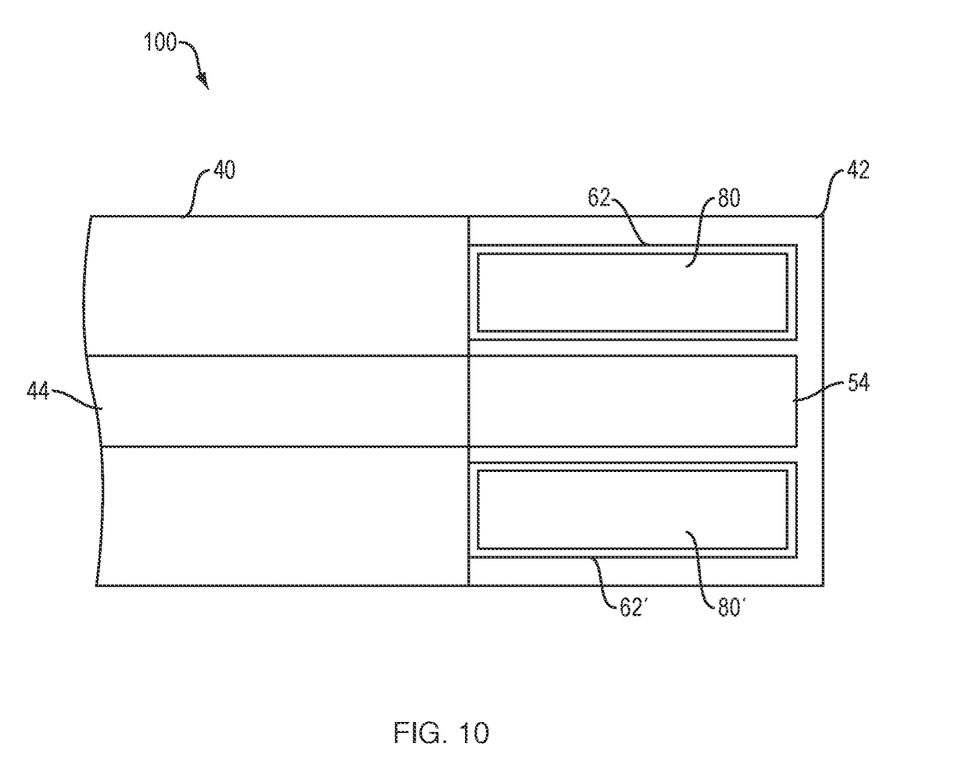
FIG. 10 is a cross-sectional view of a main catheter and cap formed in accordance with an embodiment of the present invention.
Figure 11:
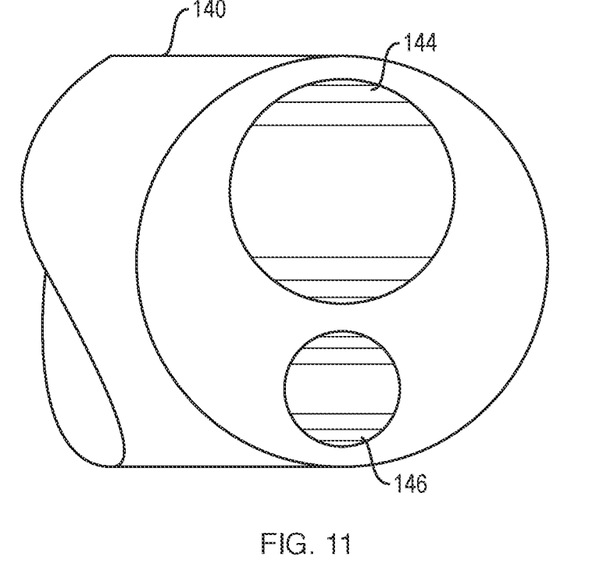
FIG. 11 is a perspective view of a portion of a distal end of a main catheter section of the device of FIG. 10.
Figure 12:
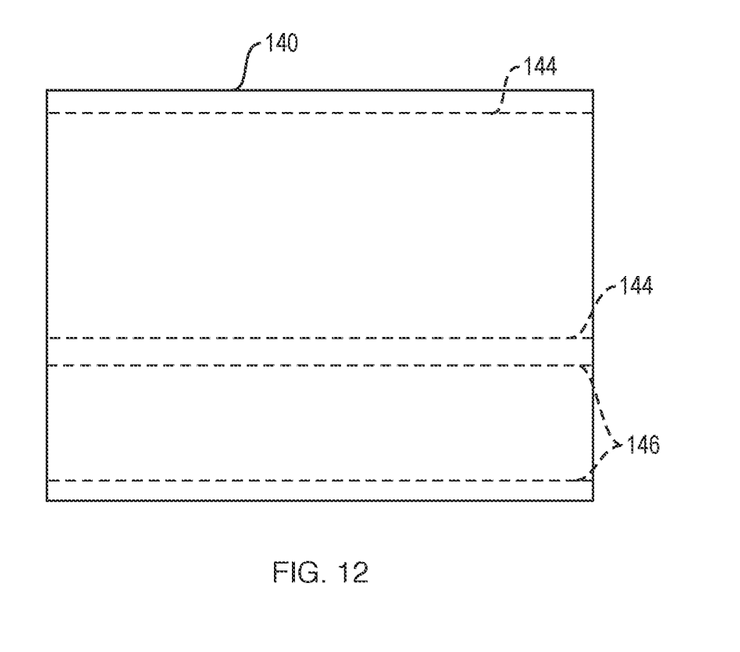
FIG. 12 is a side, x-ray view of the distal end of the main catheter section of FIG. 10.
Figure 13:
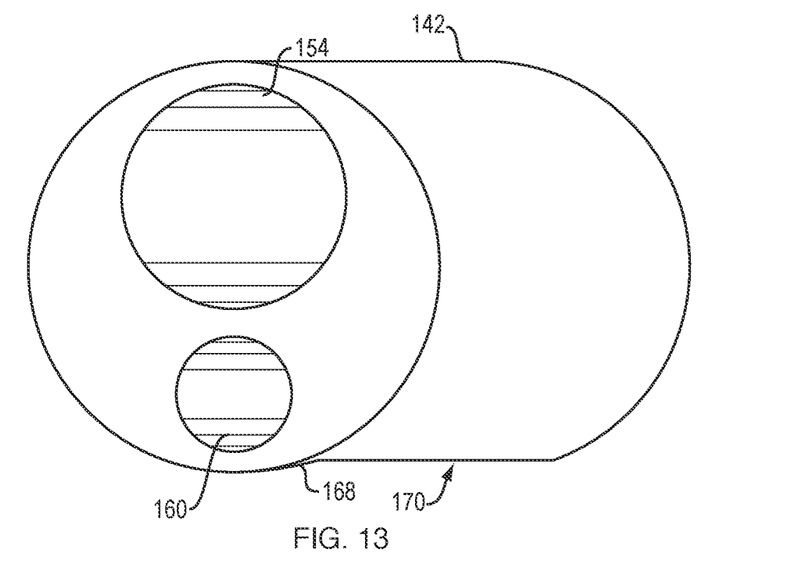
FIG. 13 is a perspective view of a proximal end of a cap section of the device of FIG. 10.
Figure 14:
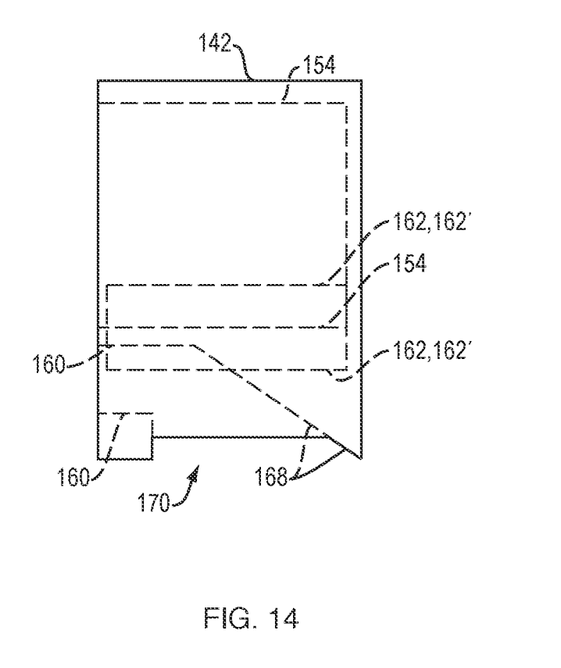
FIG. 14 is a side, x-ray view of the cap section of FIG. 10.

FIG. 9 illustrates an image 90 outputted to the display device 18. The image 90 is generated by the radial ultrasound system 16 when the insertion tube 14 with an ultrasound transducer received at the distal end are positioned within a body lumen. The image 90 shows an image with 360° of imaging features. The image 90 also includes feedback 92 identifying the orientation pins. The side port 70 is located between the orientation pins 80, 80' where the arc between the pins 80, 80' is the smallest. Thus, a user will know that any medical device exiting the side port 70 will always exit at about this smallest arc location. In the image 90, the medical device will exit the side port 70 between approximate angular values 350° to 080°. In the image 90, 000° would be at the 12 o'clock position. Therefore, if a target is identified in a radial ultrasound image, all the user needs to do in order to have the medical device interact with that target is to rotate the catheter portion 40 until the target is located within a smallest pie of the 360° image that is bordered by the orientation pins feedback 92.

As shown in FIGS. 10-14, orientation pins 180, 180' are only included in a cap section 142 and no orientation pin lumens are included in a catheter portion 140.

Figure 15:
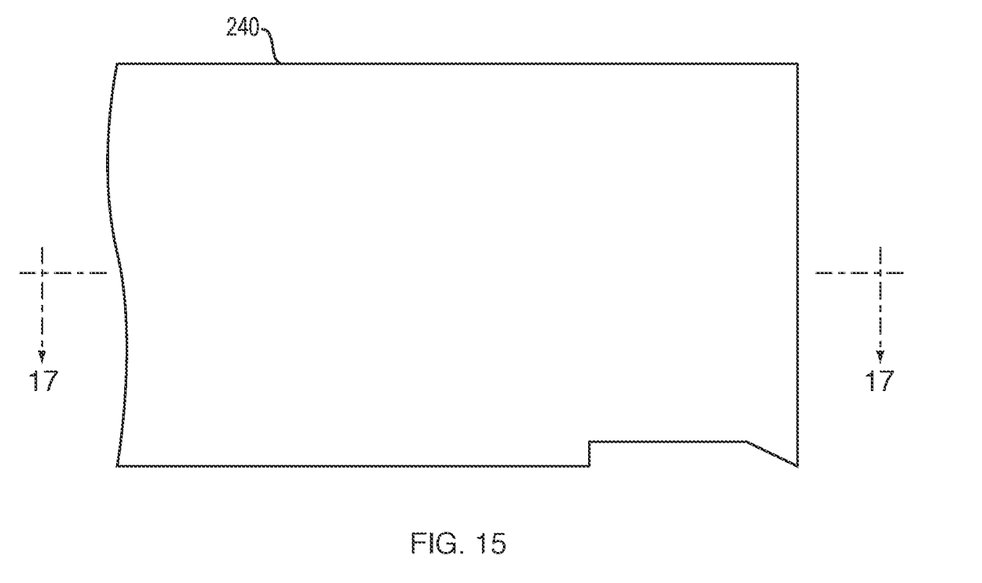
FIG. 15 is a side view of a distal end of a device formed in accordance with an embodiment of the present invention.
Figure 16:
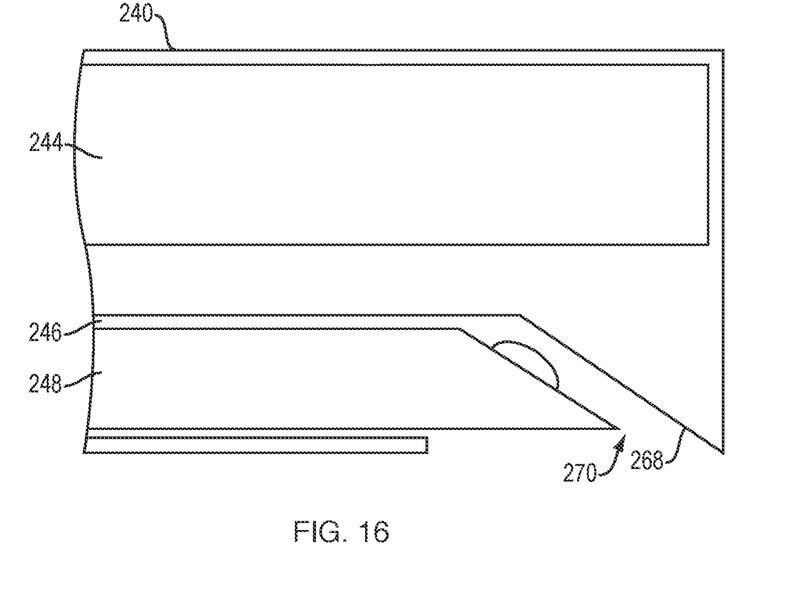
FIG. 16 is a cross-sectional view of a portion of the device shown in FIG. 15.
Figure 17:
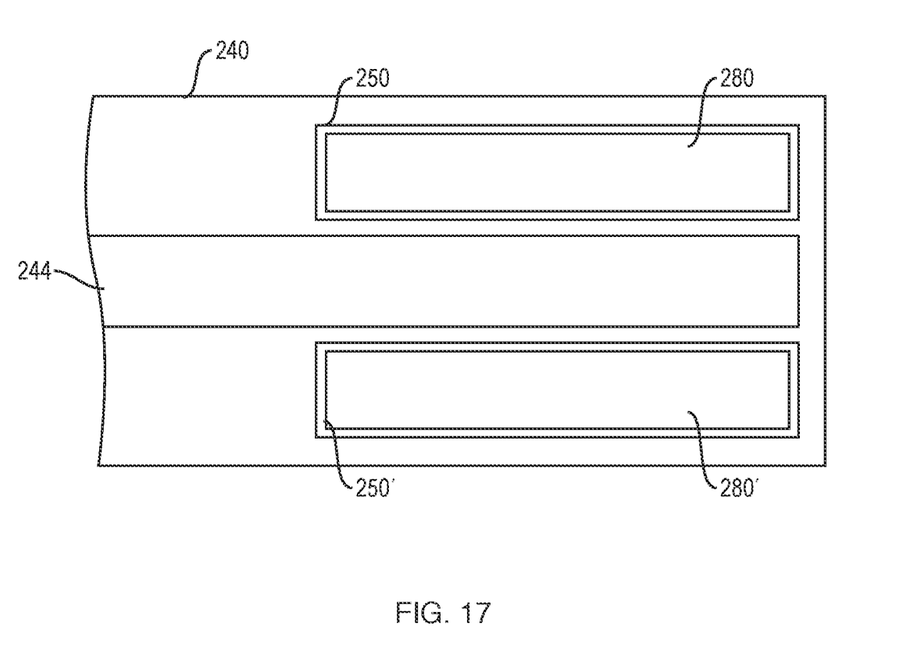
FIG. 17 is a cross-sectional view rotated 90° of the portion of the device shown in FIG. 15.

As shown in FIGS. 15-17, a catheter portion 240 does not include a cap portion. The catheter portion 240 includes at least all the features of the cap devices 42, 142 described above and features shown in the following features.

Figure 18:
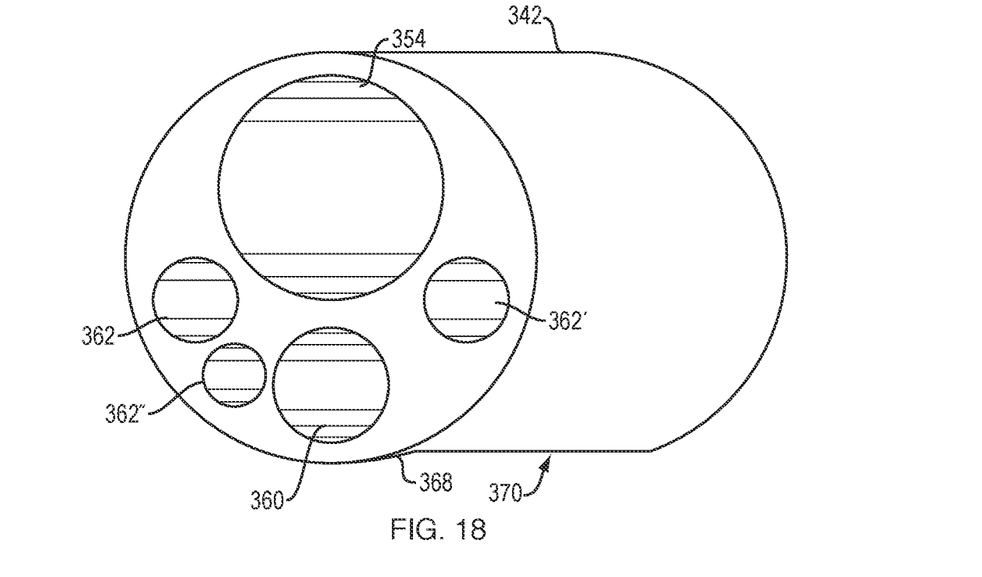
FIG. 18 is a cross-sectional, perspective view of a proximal end of a cap section of the device of FIG. 2A.
Figure 19:
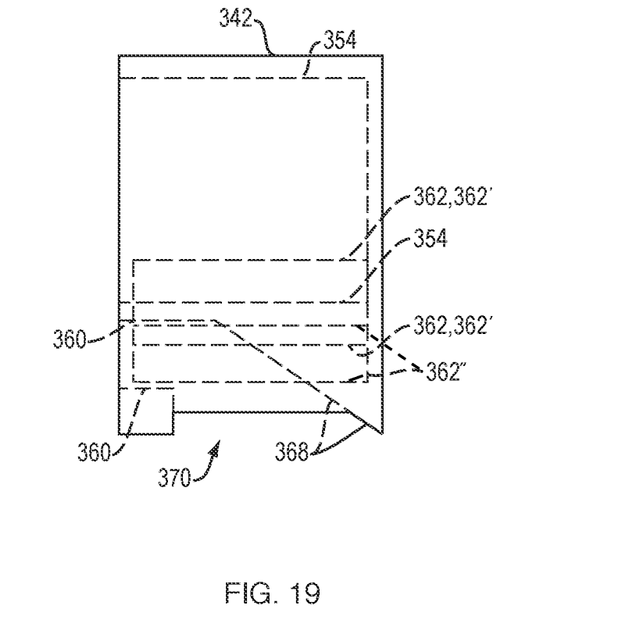
FIG. 19 is a side, x-ray view of the cap section of FIG. 18.

As shown in FIGS. 18 and 19, three orientation pins are use. Two pins are located in pin lumens 362, 362" adjacent to one another on one half of a catheter 342 and a third pin is located in a pin lumen 362' on the other half of the catheter 342. In one embodiment, the three pin lumens 362, 362', 362" may be located in the cap portion, a single catheter or both.

Any of the lumens described above may be exposed at their proximal or distal ends.

EMBODIMENTS

A. A catheter device comprising: a flexible shaft comprising: a first lumen, and a second lumen; a cap portion having a longitudinal axis, the cap portion comprising: a third lumen configured to align with the first lumen, a fourth lumen configured to align with the second lumen, an exit port, and a ramp disposed between the second lumen, of the flexible shaft, and the exit port of the cap portion; and at least one orientation pin positioned adjacent to the third lumen of the cap portion, wherein at least a portion of the third lumen, the exit port, the ramp, and the at least one orientation pin intersect a plane perpendicular to the longitudinal axis.

B. The device of A, wherein the at least one orientation pin comprises two orientation pins.

C. The device of B, wherein the two orientation pins include longitudinal axes that are positioned on the same half of the cap portion as the exit port.

D. The device of A, wherein the first lumen and the third lumen are configured to receive an ultrasound probe.

E. The device of D, wherein the second lumen and the fourth lumen are configured to receive a medical device.

F. The device of A, wherein the cap portion comprises one or more materials that are permeable to ultrasound signals.

G. The device of F, wherein the at least one orientation pin comprises one or more materials that are non-permeable to ultrasound signals.

H. A system comprising: a radial ultrasound system comprising: a radial ultrasound probe, and a signal processor configured to be in data communication with the radial ultrasound probe and generate one or more images based on data received from the radial ultrasound probe; a display device configured to present the generated one or more images; a medical device; and a catheter system comprising: a flexible shaft comprising: a first lumen configured to receive the radial ultrasound probe, and a second lumen configured to receive the medical device, a cap portion having a longitudinal axis, and at least one orientation pin. The cap portion comprising: a third lumen configured to align with the first lumen, a fourth lumen configured to align with the second lumen, an exit port, and a ramp disposed between the fourth lumen and the exit port. The at least one orientation pin is positioned adjacent to the third lumen of the cap portion, wherein at least a portion of the third lumen, the exit port, the ramp, and the at least one orientation pin intersect a plane perpendicular to the longitudinal axis.

I. The system of H, wherein the at least one orientation pin comprises two orientation pins.

J. The system of I, wherein the two orientation pins include longitudinal axes that are positioned on the same half of the cap portion as the exit port.

K. The system of H, wherein the cap portion comprises one or more materials that are permeable to ultrasound signals.

L. The system of I, wherein the at least one orientation pin comprises one or more materials that are non-permeable to ultrasound signals.

M. The system of H, wherein the generated one or more images are configured to include: an ultrasound shadow image related to the at least one orientation pin; an image feature responsive to a distal end of the medical device being disposed distal from the exit port, wherein the ultrasound shadow image and the image feature are disposed on same half of the generated one or more images.

N. A method comprising: providing a flexible shaft having a first lumen and a second lumen; providing a cap portion having a longitudinal axis, a third lumen configured to align with the first lumen, a fourth lumen configured to align with the second lumen, an exit port, and a ramp disposed between the second lumen and the exit port; providing at least one orientation pin positioned adjacent to the third lumen of the cap portion; and attaching a distal end of the flexible shaft to the proximal end of the cap portion, wherein at least a portion of the third lumen, the exit port, the ramp, and the at least one orientation pin intersect a plane perpendicular to the longitudinal axis.

O. The method of N, wherein providing at least one orientation pin comprises providing two orientation pins.

P. The method of O, wherein attaching further comprises positioning longitudinal axes of the two orientation pins on the same half of the cap portion as the exit port.

Q. The method of N, further comprising slidably receiving an ultrasound probe in the first lumen and the third lumen.

R. The method of Q, further comprising slidably receiving a medical device in the second lumen and the fourth lumen.

S. The method of N, wherein providing a cap portion comprises forming the cap portion of one or more materials that are permeable to ultrasound signals.

T. The method of S, wherein providing at least one orientation pin comprises forming the at least one orientation pin of one or more materials that are non-permeable to ultrasound signals.

The description of the invention is merely exemplary in nature and variations that do not depart from the gist of the invention are intended to be within the scope of the invention. Such variations are not to be regarded as a departure from the spirit and scope of the invention.

What is claimed is:

1. A catheter device comprising:
a flexible shaft;
a first lumen within the flexible shaft, the first lumen adapted to receive an imaging probe;

a second lumen within the flexible shaft, the second lumen including an exit port formed in a sidewall adjacent a distal end and a ramp forming the distal end of the second lumen, the ramp configured to cause a needle to extend off-axis from a portion of the catheter device that is adjacent to the exit port; and at least one echogenic orientation pin positioned adjacent to a distal end of the first lumen and aligned relative to the exit port to provide rotational orientation information about the exit port within images generated by the imaging probe; wherein at least a portion of the first lumen, the imaging probe, and the at least one echogenic orientation pin intersect a plane perpendicular to a longitudinal axis of the flexible shaft.

2. The device of claim 1, wherein the at least one echogenic orientation pin comprises two echogenic orientation pins.

3. The device of claim 2, wherein the two echogenic orientation pins include longitudinal axes that are positioned in lateral alignment along the longitudinal axis with as the exit port.

4. The device of claim 1, wherein the first lumen is configured to receive an ultrasound probe.

5. The device of claim 4, wherein the second lumen is configured to receive a medical device.

6. The device of claim 1, wherein at least a distal portion of the flexible shaft comprises one or more materials that are permeable to ultrasound signals.

7. The device of claim 6, wherein the at least one echogenic orientation pin comprises one or more materials that are non-permeable to ultrasound signals.

8. A system comprising:
an ultrasound probe, and
a signal processor configured to be in data communication with the ultrasound probe and generate one or more images based on data received from the ultrasound probe;
a display device configured to present the generated one or more images;
a medical device; and
a catheter system comprising:
a flexible shaft;
a first lumen within the flexible shaft and adapted to receive an imaging probe;
a second lumen within the flexible shaft and including an exit port formed in a sidewall adjacent a distal end and a ramp forming the distal end of the second lumen, the ramp configured to cause a needle to extend off-axis from a portion of the second lumen that is adjacent to the exit port; and
at least one echogenic orientation pin positioned adjacent to a distal end of the first lumen and aligned relative to the exit port to provide rotational orientation information about the exit port within images generated by the imaging probe;
wherein at least a portion of the first lumen, the imaging probe, and the at least one echogenic orientation pin intersect a plane perpendicular to a longitudinal axis of the flexible shaft.

9. The system of claim 8, wherein the at least one echogenic orientation pin comprises two echogenic orientation pins.

10. The system of claim 9, wherein the two echogenic orientation pins include longitudinal axes that are positioned in lateral alignment along the longitudinal axis with as the exit port.

11. The system of claim 8, wherein at least a distal portion of the flexible shaft comprises one or more materials that are permeable to ultrasound signals.

12. The system of claim 9, wherein the at least one echogenic orientation pin comprises one or more materials that are non-permeable to ultrasound signals.

13. The system of claim 8, wherein the generated one or more images are configured to include:
an ultrasound shadow image related to the at least one echogenic orientation pin;
an image feature responsive to a distal end of the medical device being disposed distal from the exit port,
wherein the ultrasound shadow image and the image feature are disposed on same half of the generated one or more images.

14. A method comprising:
providing a flexible shaft having a first lumen, a second lumen including an exit port formed in a sidewall adjacent a distal end of the flexible shaft and a ramp forming the distal end of the second lumen, the ramp configured to cause a needle to extend off-axis from a portion of the second lumen that is adjacent to the exit port, and at least one echogenic orientation pin positioned adjacent to a distal end of the first lumen;
inserting an imaging probe into the first lumen; and
generating an image of a target tissue using the imaging probe, the image including a shadow produced by the at least one echogenic orientation pin;
wherein at least a portion of the first lumen, the imaging probe, and the at least one echogenic orientation pin intersect a plane perpendicular to a longitudinal axis, and wherein the at least one echogenic orientation pin is positioned adjacent to a distal end of the first lumen and aligned relative to the exit port to provide rotational orientation information about the exit port within images generated by the imaging probe.

15. The method of claim 14, wherein providing the at least one echogenic orientation pin comprises providing two echogenic orientation pins.

16. The method of claim 15, wherein attaching further comprises positioning longitudinal axes of the two echogenic orientation pins on the same half of a cap portion as the exit port.

17. The method of claim 14, further comprising slidably receiving a medical device in the second lumen and extending the medical device out of the exit port via the ramp.

18. The method of claim 17, wherein the generating the image includes imaging a distal end of the medical device extending out of the exit port.

19. The method of claim 14, wherein providing the flexible shaft includes forming a distal portion of one or more materials that are permeable to ultrasound signals.

20. The method of claim 19, wherein providing the at least one echogenic orientation pin comprises forming the at least one echogenic orientation pin of one or more materials that are non-permeable to ultrasound signals.

* * * * *